United States Patent [19]
Westin et al.

[11] Patent Number: 4,646,726
[45] Date of Patent: Mar. 3, 1987

[54] ANKLE JOINT ORTHOSIS

[75] Inventors: Johnny Westin; Jan Karlsson, both of Umeå; Perove Abelson, Holmsund, all of Sweden

[73] Assignee: Landstingens Inkopscentral LIC, Sweden

[21] Appl. No.: 795,339

[22] Filed: Nov. 6, 1985

[30] Foreign Application Priority Data

Nov. 27, 1984 [SE] Sweden ............................ 8405969

[51] Int. Cl.$^4$ .............................................. A61F 3/00
[52] U.S. Cl. ................................................ 128/80 H
[58] Field of Search .............. 128/80 H, 80 R, 80 D, 128/80 E, 80 J

[56] References Cited

U.S. PATENT DOCUMENTS

| | | | |
|---|---|---|---|
| 1,058,322 | 4/1913 | Mueller | 128/80 H |
| 2,847,991 | 8/1958 | Andrews | 128/80 E |
| 4,102,337 | 5/1978 | Golia | 128/80 E |
| 4,289,122 | 9/1981 | Mason et al. | 128/80 H X |
| 4,517,968 | 5/1985 | Greene et al. | 128/80 H |
| 4,556,054 | 12/1985 | Paulseth | 128/80 H |

Primary Examiner—Clifford D. Crowder
Attorney, Agent, or Firm—Ostrolenk, Faber, Gerb & Soffen

[57] ABSTRACT

The present invention relates to an ankle joint orthosis (1), which consists of an ankle part (2) that is fixed around the lower leg, and a foot plate (3), which is placed against the sole of the foot. The foot plate (3) and the ankle part (2) are on one side connected with each other by a pivot joint (6) and on the other side connected with each other by two straps (7, 8). The first strap (7) extends essentially vertically from the ankle part (2) to the foot plate (3), whereon it is fixed, whereas the second strap (8) from a common junction (9) extends obliquely to the front part of the foot plate (3). From the common junction (9) a third strap (10) originates, which is braced by a clasp (11) being arranged on the ankle part (2).

11 Claims, 1 Drawing Figure

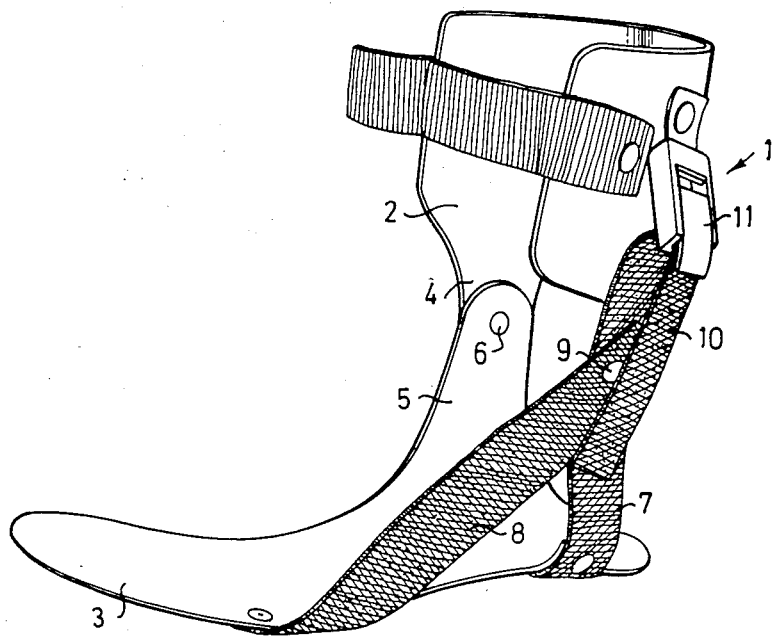

ANKLE JOINT ORTHOSIS

DESCRIPTION

The present invention relates to an ankle joint orthosis comprising an ankle part, which is fastened around the lower part of the lower leg, and a foot plate being movably connected with said ankle part.

Ankle joint orthoses of this kind are used in order to support the instep, for instance when the ligaments of the instep are slackened, or the joint for some other reason needs a stabilisation in lateral direction. Orthoses are also used for preventive purposes, particularly for persons tending to sprain, or in medical treatment, for example after a surgical operation, in order to relieve the ligaments.

In an earlier-known ankle joint orthosis the ankle part is by two pivots, being located outside and inside, respectively of the leg, rather rigidly connected with the foot plate. It is thereby nearly impossible to arrange the pivot joints in an ideal manner, i.e. so that the rotation axes of the orthosis and the ankle joint, respectively coincide. This requires in fact, firstly an extremely careful and time-consuming, and therefore costly, individual fitting of the orthosis for each bearer, and secondly that, each time the orthosis shall be applied, great pains are taken to fit it into exact position on the bearer. If the ideal fixation cannot be attained, which mostly is the case, the orthosis will either essentially immobilise the ankle part, or it will on each turning occasion move relative to the bearer and this may cause chafes and give the bearer pain.

The purpose of the present invention is to eliminate these drawbacks. This is achieved by an ankle joint orthosis of the kind mentioned at the beginning, thereby that the foot plate on the inside of the foot via a pivot joint is connected with the ankle part, and on its outside is connected with the ankle part by aid of at least one elongated, flexible means being in the main inextensible in longitudinal direction.

By shaping the orthosis in this manner, it will provide the ankle joint with a steady support in lateral direction and simultaneously allow a certain freedom of movement in this direction, so that the natural motion process of the joint is not prevented, but that there occurs a relative movement between the ankle joint orthosis and the lower leg.

The invention is exemplified by an embodiment under reference to the sole drawing, which shows a perspective view of an ankle joint orthosis.

The ankle joint orthosis 1 comprises an ankle part 2, which is attached around the lower part of the lower leg, and a foot plate 3, fitting snugly to the foot, for instance within a shoe. The ankle part 2 and the foot plate 3 are made of a material which is rather rigid, but nevertheless has a certain flexibility, for example a suitable plastic, which permits that the ankle part 2 can be adapted to different sizes of the lower leg and be fixed by straps, Velcro tape arrangements, adhesive strips or the like. The ankle part 2 can be padded on the inside, or be provided with a soft lining to increase the comfort of the bearer. The ankle part 2 is provided with a projection 4 directed towards the foot plate 3, and the foot plate 3 is provided with a projection 5 directed towards the ankle part 2. The projections are connected with each other by a pivot joint 6. The projections are rather rigid, but have a certain flexibility in lateral direction. On the opposite side of the foot, the outside, the foot plate 3 is connected to the ankle part 2 by aid of two rather inextensible straps 7, 8, i.e. they have a very delimited extensibility in longitudinal direction. One of the straps 7 is fastened in the foot plate and extends in the main vertically up towards the ankle part 2. The second strap 8 is fastened further at the front of the foot plate 3 and is inclined upwards to the first strap 7 towards a common junction 9. From the junction 9 a third strap 10 extends to a clasp 11 by which the effective length of the third strap 10 can be controlled, whereby also the clamping force of the straps 7 and 8 can be controlled.

The junction 9 can approximately cooresspond to the joint point 6 for good mobility and stability. In other embodiments of the invention straps 7 and 10 can consist of the same strap. Strap 8 can also be fastened direct to the ankle part 2, possibly by a clasp corresponding to 11. Hereby an other possibly adjustable restriction of the mobility is obtained as when strap 8 is connected to point 9.

By the above described ankle joint orthosis the instep has a steady, but somewhat flexible support in lateral direction, so that the natural joint is not immobilised and the device simultaneously is well fixed thereon without chafing.

We claim:

1. An ankle joint orthosis comprising an ankle part, which is fastenable on the lower part of the lower leg, and a foot plate being movably connected to the ankle part, wherein the foot plate is connected adjacent the lower leg via a pivot joint to the ankle part and on the opposite side of the foot is connected to the ankle part by at least two elongated flexible means being generally inextensible in the longitudinal direction, wherein the first flexible means extend essentially vertically from the ankle part to the foot plate, and the second flexible means extends inclined at an angle from the ankle part to the front part of the foot plate.

2. An ankle joint orthosis according to claim 1, wherein the length of the flexible means is adjustable.

3. An ankle joint orthosis according to claim 2, wherein the flexible means originate from a common junction on the ankle part.

4. An ankle joint orthosis according to claim 3, wherein the common junction approximately corresponds to the position of the ankle joint.

5. An ankle joint orthosis according to claim 3, wherein a third flexible means extending from the common junction to a clamping means arranged on the ankle part is provided, by which clamping means the effective length of the third flexible means is adjustable.

6. An ankle joint orthosis according to claim 5, wherein the third flexible means consists of an elongation of the first flexible means.

7. An ankle joint orthosis according to claim 1 or 2, wherein the first and the second means each separately, are connected to the ankle part.

8. An ankle joint orthosis according to claim 7, wherein each flexible means via its own clasp is connected to the ankle part, so that the length of each flexible means is individully adjustable.

9. An ankle joint orthosis according to claim 1, wherein the flexible means consist of straps.

10. An ankle joint orthosis according to claim 1, wherein the ankle part and the foot plate consist of a rather rigid, but nevertheless flexible material.

11. An ankle joint orthosis according to claim 10, wherein the material consists of a plastic.

* * * * *